US009271945B2

(12) United States Patent
Hurley

(10) Patent No.: US 9,271,945 B2
(45) Date of Patent: Mar. 1, 2016

(54) DERMAL PAIN RELIEF DELIVERY SYSTEM

(71) Applicant: Maureen Ann Hurley, Tucson, AZ (US)

(72) Inventor: Maureen Ann Hurley, Tucson, AZ (US)

( * ) Notice: Subject to any disclaimer, the term of this patent is extended or adjusted under 35 U.S.C. 154(b) by 0 days.

(21) Appl. No.: 14/614,308

(22) Filed: Feb. 4, 2015

(65) Prior Publication Data
US 2015/0216815 A1  Aug. 6, 2015

Related U.S. Application Data

(60) Provisional application No. 61/965,625, filed on Feb. 4, 2014.

(51) Int. Cl.
| | |
|---|---|
| *A61F 13/00* | (2006.01) |
| *A61L 15/16* | (2006.01) |
| *A61F 13/02* | (2006.01) |
| *A61K 9/70* | (2006.01) |
| *A61K 47/34* | (2006.01) |
| *A61K 31/167* | (2006.01) |
| *A61K 31/245* | (2006.01) |
| *A61K 31/5375* | (2006.01) |
| *A61K 31/445* | (2006.01) |

(52) U.S. Cl.
CPC ............ *A61K 9/7084* (2013.01); *A61K 31/167* (2013.01); *A61K 31/245* (2013.01); *A61K 31/445* (2013.01); *A61K 31/5375* (2013.01); *A61K 47/34* (2013.01)

(58) Field of Classification Search
None
See application file for complete search history.

(56) References Cited

U.S. PATENT DOCUMENTS

| 6,496,727 B1* | 12/2002 | Bernhard | ................. | A61N 1/30 604/20 |
|---|---|---|---|---|
| 2009/0048296 A1* | 2/2009 | Campbell | ............ | A61K 9/0014 514/312 |
| 2010/0292660 A1* | 11/2010 | Kydonieus | ............. | A61K 9/703 604/307 |

OTHER PUBLICATIONS

NPL/Google search results; downloaded Sep. 1, 2015.*

* cited by examiner

*Primary Examiner* — Jeffrey T Palenik

(57) ABSTRACT

An easy to apply dermal delivery system embodying an apparatus and a method for relieving the localized discomfort caused by footwear is provided. The delivery system may include a generally planar base, adhesive layer and delivery apparatus. The base forms a basic recess on one side, whereby the non-recessed portion provides a basic framework along the periphery thereof. The adhesive layer overlaid the recessed-side of a similarly shaped base forms an adhesive recess and an adhesive framework. The delivery apparatus may be sized and shaped to substantially fill the adhesive recess and be substantially flush with a top side of the adhesive framework. The delivery apparatus may include a film, housing and/or impregnated with a plurality of anesthetic components, wherein the film is adapted for dermal delivery of the plurality of anesthetic components, while the adhesive framework removably attaches the delivery system to a user.

9 Claims, 2 Drawing Sheets

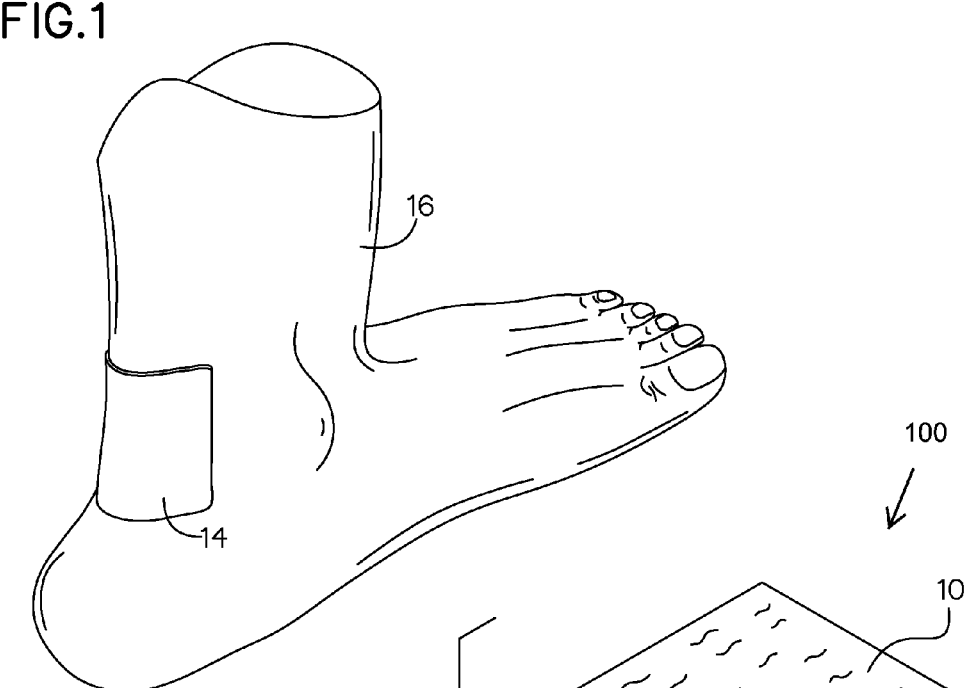
FIG.1
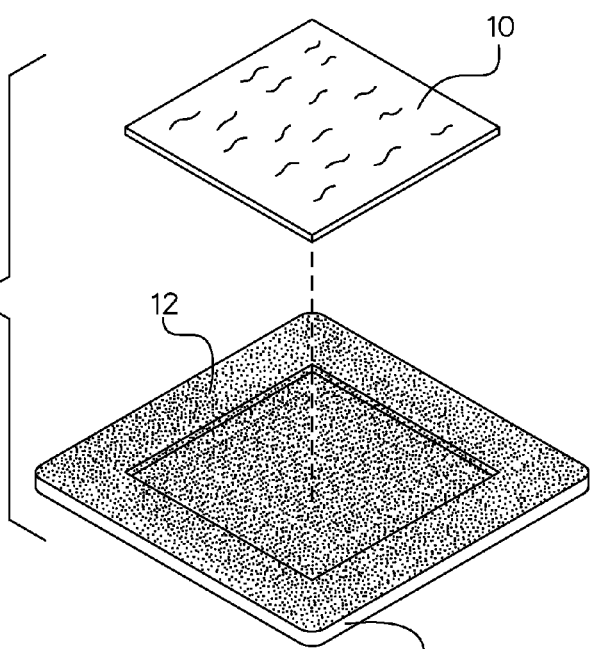
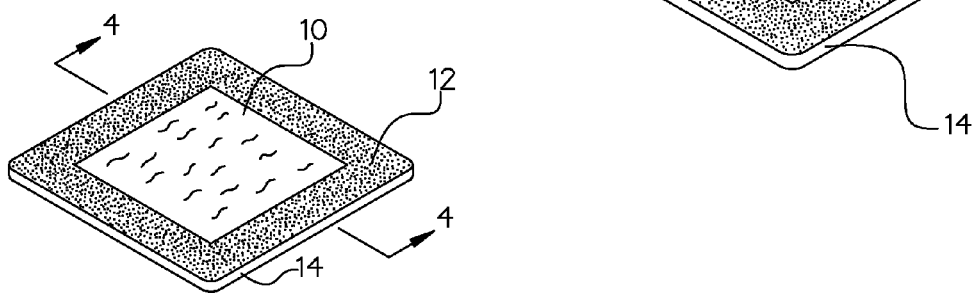
FIG.3
FIG.2

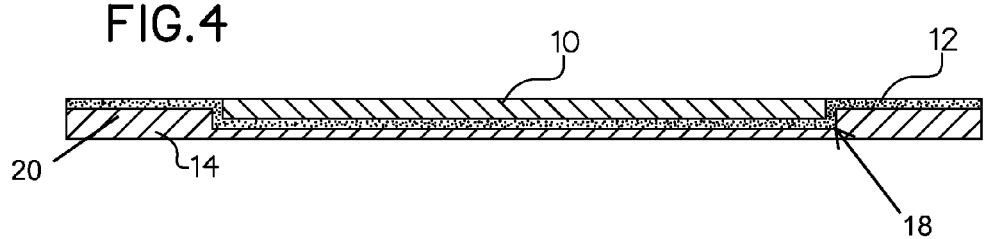
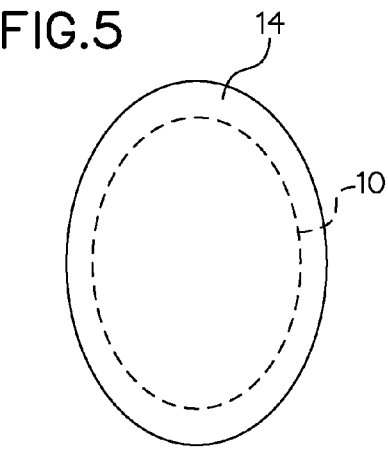
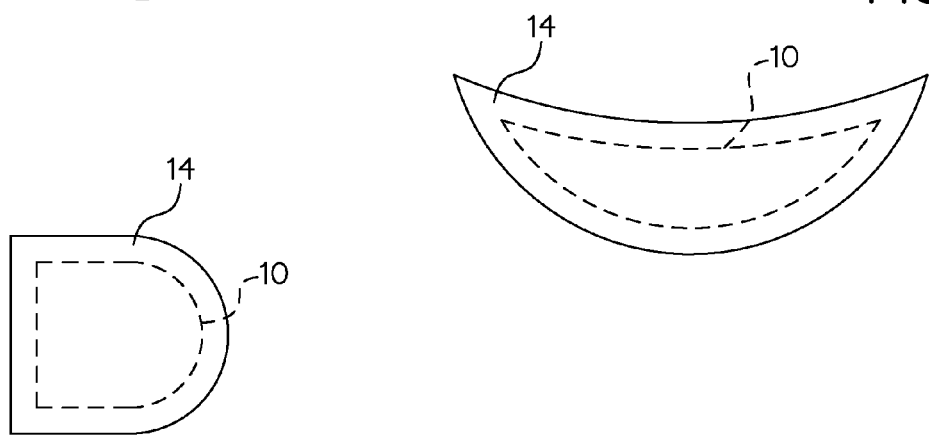

DERMAL PAIN RELIEF DELIVERY SYSTEM

CROSS-REFERENCE TO RELATED APPLICATION

This application claims the benefit of priority of U.S. provisional application No. 61/965,625, filed Feb. 4, 2014, the contents of which are herein incorporated by reference.

BACKGROUND OF THE INVENTION

The present invention relates to pain relief and, more particularly, to an easy to apply dermal delivery system embodying an apparatus and a method for relieving the localized discomfort caused by footwear.

Currently there are a number of solutions for discomfort caused by the shape, size and material of footwear, typically fashionable shoes, such as high heels, wedge shoes and the like. Usually such discomfort is localized at impingement locations, where the footwear presses against that portion of wearer's foot. Currently, however, there are no truly effective solutions for such localized discomfort. Some of the current devices, such as insoles and inserts, are bulky, contributing to additional pressure at the impingement locations, in addition to being unflattering when used with the usual suspects of fashionable shoes. Another current solution is topical sprays. Unfortunately, being aerosol-based or the like, such sprays are ineffective for targeted delivery to impingement locations; moreover, such sprays require frequent re-application because of their evanescent nature. Yet another current solution is the application of bandage or mole skin, which merely acts as a barrier but does not delivery relief to the ongoing pain nor allows the wearer to extend the length of time the fashionable shoe can be worn pain-free.

As can be seen, there is a need for an easy to apply dermal delivery system embodying an apparatus and a method for relieving the localized discomfort caused by footwear.

SUMMARY OF THE INVENTION

In one aspect of the present invention, an easy to apply, re-usable dermal delivery system for relieving localized discomfort comprises a planar base having a first side and a second side, wherein the second side forms a basic recess, resulting in a basic framework along the periphery of the basic recess; a planar, two-sided adhesive layer of substantially similar shape as the second side of the base; and a delivery apparatus comprising a delivery film providing a plurality of anesthetic components, wherein the delivery apparatus is shaped to substantially fill the basic recess substantially layered with the adhesive layer.

In another aspect of the present invention, an easy to apply, re-usable dermal delivery system for relieving localized discomfort comprises a planar base having a first side and a second side, wherein the first side provides a skin-tone colored barrier, and wherein the second side forms a basic recess, resulting in a basic framework along the periphery of the basic recess; a planar, two-sided adhesive layer of substantially similar shape as the second side of the base, wherein the adhesive layer overlays a substantial portion of the second side of the base, forming an adhesive recess and a surrounding adhesive framework; and a delivery apparatus comprising a PET release liner configured for dermal delivery of a plurality of anesthetic components, and wherein the delivery apparatus is shaped to substantially fill the adhesive recess.

These and other features, aspects and advantages of the present invention will become better understood with reference to the following drawings, description and claims.

BRIEF DESCRIPTION OF THE DRAWINGS

FIG. 1 is a perspective view of an exemplary embodiment of the present invention, shown in use;

FIG. 2 is a perspective view of an exemplary embodiment of the present invention;

FIG. 3 is an exploded view of an exemplary embodiment of the present invention

FIG. 4 is a section view of an exemplary embodiment of the present invention, taken along line 4-4 in FIG. 2;

FIG. 5 is a top view of an exemplary embodiment of the present invention;

FIG. 6 is a top view of an exemplary embodiment of the present invention; and

FIG. 7 is a top view of an exemplary embodiment of the present invention.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides an easy to apply dermal delivery system embodying an apparatus and a method for relieving the localized discomfort caused by footwear. The delivery system may include a generally planar base, adhesive layer and delivery apparatus. The base forms a basic recess on one side, whereby the non-recessed portion provides a basic framework along the periphery thereof. The adhesive layer overlaid the recessed-side of a similarly shaped base forms an adhesive recess and an adhesive framework. The delivery apparatus may be sized and shaped to substantially fill the adhesive recess and be substantially flush with a top side of the adhesive framework. The delivery apparatus may include a film, housing and/or impregnated with a plurality of anesthetic components, wherein the film is adapted for dermal delivery of the plurality of anesthetic components, while the adhesive framework removably attaches the delivery system to a user.

Referring to FIGS. 1 through 7, the present invention provides an easy to apply dermal delivery system 100 embodying a delivery apparatus 10 and a method for relieving the localized discomfort caused by footwear. The delivery apparatus 10 is adapted to topically deliver a local anesthetic to an impingement location, whereby the wearer 16 may extend the length of time the uncomfortable footwear can be worn without pain. The impingement location may include where the footwear applies pressure to the skin of the wearer 16.

The delivery system 100 may include a base 14, an adhesive layer 12 and the delivery apparatus 10. The base 14 may be generally planar having a first side and a second side. The first side may be substantially uniform in shape and be any suitable color, including skin-tones as well as fanciful colours. The second side may form a basic recess 18 whereby the non-recessed portion of the second side provides a resulting basic framework 20 along the periphery of the basic recess 18, as illustrated in FIG. 4.

The base 14 may be generally planar and made of foam, silicone or other suitably comfortable, durable materials. The base 14 and the basic recess 18 may be any shape and size, as illustrated in FIGS. 5 through 7, suitable for application along the skin of the wearer so as to bring the delivery apparatus 10 into contact with the impingement location while providing a suitable thin barrier between the footwear and the skin of the wearer 16.

The adhesive layer 12 may be a two-sided adhesive material having substantially the same shape and size as the second side of the base 14 so as to overlay at least a substantial portion of the basic recess 18 and a substantial portion of the basic framework 20. When the adhesive layer 12 is overlaid on the second side of the base 14, an adhesive recess and an adhesive framework are provided.

The delivery apparatus 10 may be sized and shaped to substantially fill the adhesive recess and be substantially flush with a top side of the adhesive framework. The delivery apparatus 10 may include a film, PET release liner or the like that houses and/or is impregnated with a plurality of anesthetic components. The plurality of anesthetic components may include, but not be limited to, Lidocaine, ranging from approximately 4% through 4.75%, in an aqueous base, benzocaine, prilocaine, tetracaine, proxymetacaine, pramoxine, buprivacaine, oxybuprocain, butamben, glycerin, D-sorbitol, propylene glycol, polyvinyl alcohol, urea, sodium polyacrylate, carboxymethylcellulose sodium, gelatin, polyacrylic acid, kaolin, tartaric acid, dihydroxyaluminum aminoacetate, methylparaben (preservative), propylparaben (preservative), edetate disodium, and the like. The film, PET release liner, and the like may be adapted for dermal delivery of the plurality of anesthetic components where the delivery apparatus 10 contacts the skin/impingement location of the wearer 16.

A method of using the present invention may include the following. The delivery system 100 disclosed above may be provided. The wearer 16 may removably secure the delivery apparatus 10 in the adhesive recess. The wearer 16 may removably secure the adhesive framework about the impingement location or location of discomfort on their skin so as to interface the delivery apparatus 10 and the impingement location or location of discomfort, wherein the plurality of anesthetic components may be delivered thereto, and the first side acts as a barrier viz-a-viz the footwear. After a predetermined period, the wearer 16 may remove the used delivery apparatus 10 and replace it with a new, unused delivery apparatus 10 for reattachment about the same or new the impingement location or location of discomfort, thereby enabling a re-useable base 14 and/or adhesive layer 12.

In certain embodiments, the user may apply the delivery system 100 to other areas of the body besides the feet. For example, the delivery apparatus 10 may be secured between the skin and an uncomfortable article of clothing, such as a bra strap.

It should be understood, of course, that the foregoing relates to exemplary embodiments of the invention and that modifications may be made without departing from the spirit and scope of the invention as set forth in the following claims.

What is claimed is:

1. An easy to apply, re-usable dermal delivery system for relieving localized discomfort, comprising:
    a base having a planar first side and a second side, wherein the second side forms a basic recess having a basic recess surface parallel to and disposed between both the first side and the second side;
    a planar two-sided adhesive layer having a first adhesive side and a second adhesive side, wherein the first adhesive side adheres to both the second side and the basic recess surface so as to form an adhesive recess surface parallel to and disposed between both the basic recess surface and the second adhesive side, wherein the base and the two-sided adhesive layer substantially share a periphery; and
    a delivery apparatus comprising a delivery film providing a plurality of anesthetic components, wherein the delivery apparatus is removably adhered the adhesive recess surface.

2. The dermal delivery system of claim 1, wherein the delivery apparatus is dimensioned to extend from the adhesive recess surface so as to terminate substantially at a plane defined by the second adhesive side.

3. The dermal delivery system of claim 1, wherein the delivery film is a PET release liner.

4. The dermal delivery system of claim 1, wherein the delivery film is configured for dermal delivery of the plurality of anesthetic components.

5. The dermal delivery system of claim 1, wherein plurality of anesthetic components comprises Lidocaine in an aqueous base.

6. The dermal delivery system of claim 5, wherein the percentage of Lidocaine ranges from approximately 4% to approximately 4.75%.

7. The dermal delivery system of claim 1, wherein plurality of anesthetic components comprises benzocaine, prilocaine, tetracaine, proxymetacaine, pramoxine, buprivacaine, oxybuprocain, butamben, glycerin, D-sorbitol, propylene glycol, polyvinyl alcohol, urea, sodium polyacrylate, carboxymethylcellulose sodium, gelatin, polyacrylic acid, kaolin, tartaric acid, dihydroxyaluminum aminoacetate, methylparaben, propylparaben, and edetate disodium.

8. The dermal delivery system of claim 5, wherein the first side provides a skin-tone colored barrier.

9. The dermal delivery system of claim 2, wherein the delivery apparatus is dimensioned to substantially fill a space defined by the adhesive recess surface and the plane defined by the second adhesive side.

* * * * *